United States Patent [19]

Weyn

[11] 4,211,341

[45] * Jul. 8, 1980

[54] DISPENSING CONTAINER OF STABILIZED EXTRUDABLE DENTIFRICE CONTAINING NORMALLY CHEMICALLY REACTIVE COMPONENTS

[75] Inventor: Hendrik F. Weyn, Le Chesnay, France

[73] Assignee: Colgate-Palmolive Company, New York, N.Y.

[ * ] Notice: The portion of the term of this patent subsequent to Jul. 4, 1995, has been disclaimed.

[21] Appl. No.: 876,709

[22] Filed: Feb. 10, 1978

Related U.S. Application Data

[63] Continuation-in-part of Ser. No. 714,736, Aug. 16, 1976, Pat. No. 4,098,435.

[51] Int. Cl.$^2$ ............................................. B65D 35/22
[52] U.S. Cl. ......................................................... 222/94
[58] Field of Search ............... 222/94, 107, 145, 394, 222/92, 215, 386; 206/219; 53/474, 467; 128/216, 272

[56] References Cited

U.S. PATENT DOCUMENTS

| | | | |
|---|---|---|---|
| 2,982,396 | 5/1961 | Shihadeh | 206/219 |
| 3,002,658 | 10/1961 | Sauda | 222/94 |
| 3,335,912 | 8/1967 | Reeves | 222/94 |
| 4,098,435 | 7/1978 | Weyn | 222/94 |

*Primary Examiner*—Stanley H. Tollberg
*Attorney, Agent, or Firm*—Robert L. Stone; Murray M. Grill; Herbert S. Sylvester

[57] ABSTRACT

A stabilized and extrudable paste or gel dentifrice comprises two dentifrice portions, each of which includes a component which is chemically reactive with the other such component in the other portion, with the portions being maintained separate from each other in a dispensing container from which they are dispensable together through a closable opening therein in response to pressure. One of the reactive compounds may be an alkali metal fluorine-containing salt such as sodium fluoride or sodium monofluorophosphate, used for its effect in hardening tooth enamel, and the other may be a water insoluble calcium salt, such as dicalcium phosphate, tricalcium phosphate or calcium carbonate, used as a polishing agent. To improve storage stability of the dentifrice such dentifrice portions are separated by an extrudable material, such as a polyhydric alcohol-water gel of a gum, e.g., sodium carboxymethyl cellulose. Also within the invention are various methods for the manufacture of the mentioned dentifrices.

27 Claims, 6 Drawing Figures

Fig. 1.
Fig. 3.
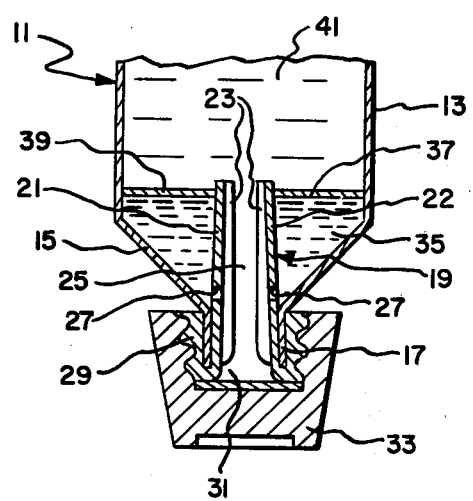
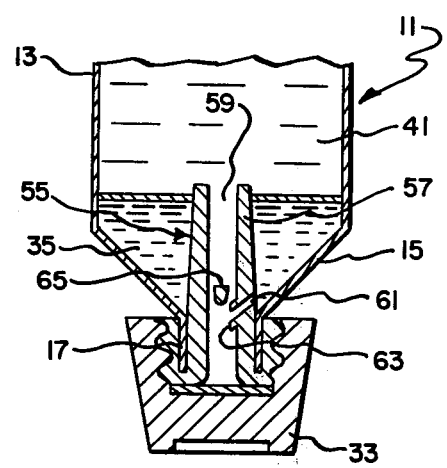
Fig. 2.
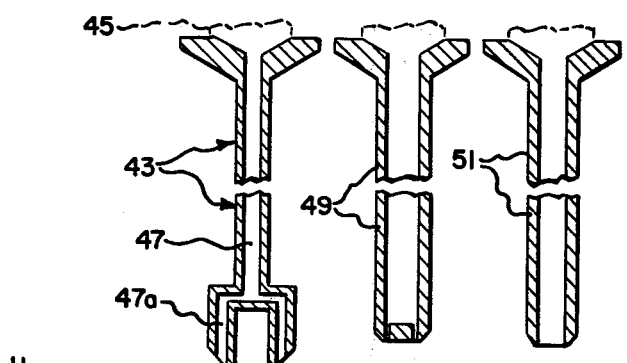
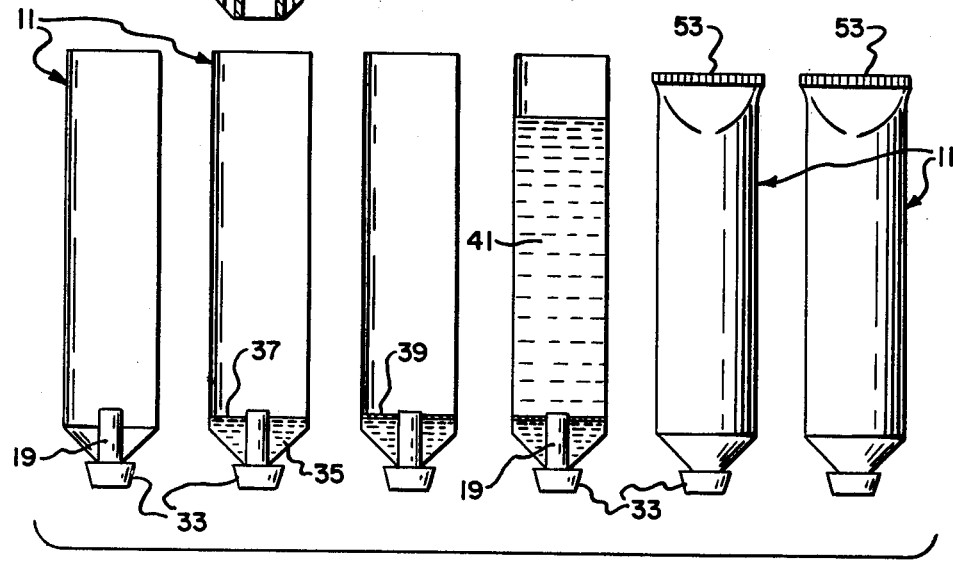

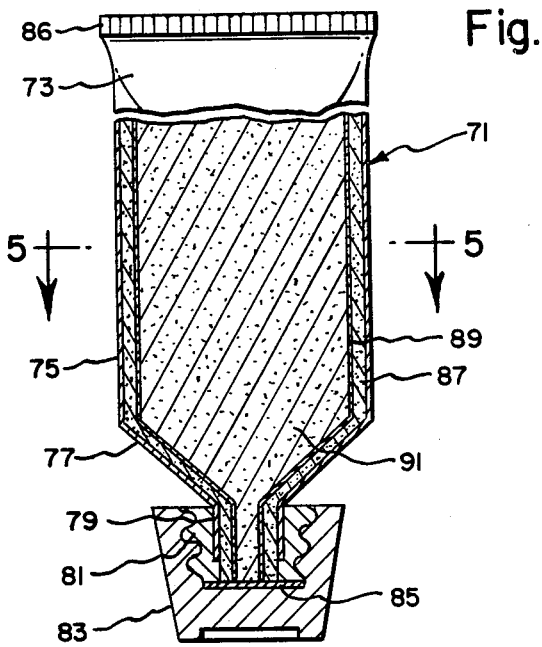
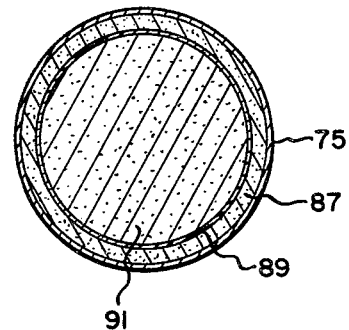
Fig. 4.
Fig. 5.
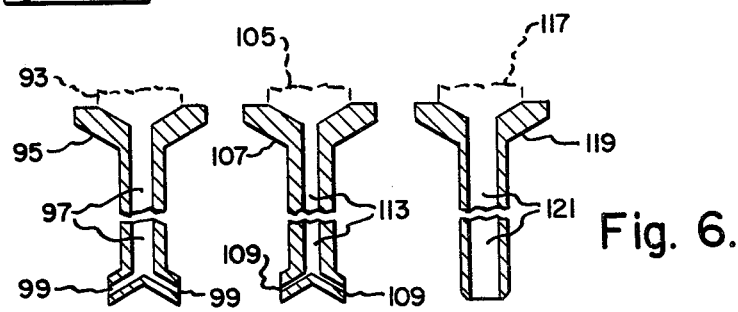
Fig. 6.
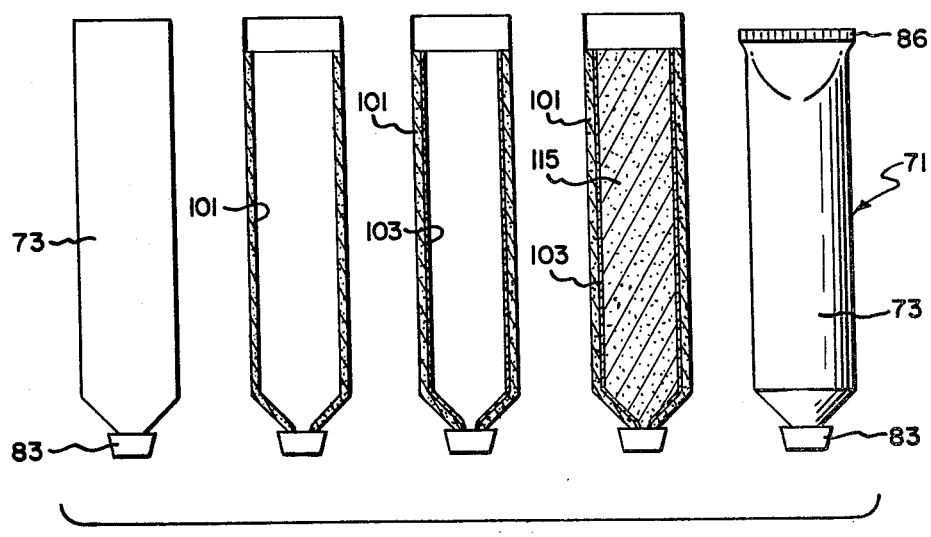

DISPENSING CONTAINER OF STABILIZED EXTRUDABLE DENTIFRICE CONTAINING NORMALLY CHEMICALLY REACTIVE COMPONENTS

This application is a continuation-in-part of my application Ser. No. 714,736 filed Aug. 16, 1976 which is now U.S. Pat. No. 4,098,435 for Stabilized Dentifrice Containing Initially Physically Separated Normally Reactive Components, granted July 4, 1978.

This invention relates to stabilized packaged dentifrices containing normally reactive components. More particularly, it relates to such a dentifrice in a dispensing container with reactive portions packaged so as to be dispensable together but to remain separate during storage before intended use. The invention also includes methods of making such products.

Dentifrice compositions in paste, gel or cream form are well known and are conventionally dispensed from collapsible tubes by applications of compressing finger pressures on the tubes. "Aerosol" or pressure packed dentifrice compositions have been marketed and "squeeze-bottle" containers, usually made of resilient synthetic organic polymeric material, e.g., polyethylene, may be used to dispense dentifrices. The tubes employed in the prior art are usually of thin aluminum although other deformable metal tubes (which are non-resilient) may also be employed. In th past tin and lead tubes were used but if suitable protective linings, usually of "plastic", are present, various other metals are also useful. Resilient synthetic organic polymeric plastic tubes have been used but have not been as popular as the collapsible metal tubes.

Although most dentifrices are opaque and white, in recent years clear gels have been marketed and colored dentifrices have found favor in the marketplace. Striped dentifrices have been produced by utilizing any of a variety of filling and dispensing means, which means usually operate by discharging simultaneously in orderly manner a white dentifrice and a colored dentifrice or by "mixing" differently colored dental products, either as the tube is filled or as the dentifrice is dispensed, so as to result in a striped, extruded product.

The importance of fluoride treatments for hardening tooth enamel and fighting tooth decay has been recognized almost universally within recent years and dentifrice compositions containing fluorides have been marketed and have been found to be effective products, the repeated use of which helps to harden tooth enamel and inhibit tooth decay. Yet, the effectiveness of soluble fluorine-containing compounds, such as sodium monofluorophosphate and sodium fluoride or mixtures thereof, has been limited by the reactivity of such compounds with other components of normal dentifrice compositions, such as calcium or other alkaline earth or heavy metal compounds, especially those which are soluble or slightly soluble in the medium, e.g., water, employed and which produce insoluble reaction products when they react with such a soluble flourine-containing compound. Even essentially insoluble (usually water insoluble) salts, such as calcium phosphates, and other "insoluble" polishing agents in which the metal component thereof is an alkaline earth metal or a heavy metal, can adversely chemically react with the mentioned fluorine-containing compounds. Additionally, various dentifrice components, such as quaternary ammonium salt bactericides, soluble aluminum and zinc salts (which act as astringents), mild acids or acid-forming materials for producing gradual pH changes in the mouth during tooth brushing and effervescent or bubble-releasing materials, often have to be omitted from dentifrice formulations due to undesirable reactions thereof with other dentifrice components using storage. Accordingly, there has been a need for dentifrices in which normally reactive materials may be included but in which they do not undergo objectionable chemical reactions during storage. Thus for example, important improvements in utility result when one is able to employ normally reactive components in a dentifrice composition so that they can be dispensed together readily from an economical single container. Such a container of dentifrice is an embodiment of the present invention.

In accordance with this invention a stabilized cream, paste or gel dentifrice comprises at least two components which are normally reactive with each other and which are in dentifrice portions kept separate from each other in a dispensing container having a closable opening through which said portions and compounds are dispensable together by pressure. Each of the two mentioned components is in a dentifrice portion in a different part of the container, held apart from the other portion and the storage stability of the product is increased by having an extrudable separator between them. The dentifrice, when extruded, is preferably homogeneous in appearance (although really composed of separate material "streams"). It is usually of one color and that color is preferably white.

The invention will be readily understood by reference to the preceding and the following description, taken in conjunction with the drawing in which:

FIG. 1 is a vertical central sectional elevation of a dispensing end of a tube of the present stabilized packaged dentifrice;

FIG. 2 is a somewhat schematic illustration partly in central sectional vertical elevation of the manufacture of the present stabilized packaged dentifrice, showing the filling of reactive dentifrice portions into dispensing tubes containing blending means;

FIG. 3 is a central sectional vertical elevation of a modification of the product of FIG. 1, showing the movement of a reactive dentifrice portion to the interior of a ribbon of dentifrice being dispensed;

FIG. 4 is a partial central sectional elevation of a dispensing container exteriorly resembling those already described but in which the blending fitting has been eliminated and the reactive dentifrice portions are concentrically disposed about the tube axis with an extrudable separator between them;

FIG. 5 is a sectional horizontal plan along plane 5—5 of FIG. 4; and

FIG. 6 is a somewhat schematic illustration, partly in central sectional elevation, showing the manufacture of a dispensing container of stabilized dentifrice of this invention, including the filling of reactive dentifrice portions into separate parts of dispensing tubes with an extrudable separator between them.

Collapsible dispensing tube 11 has a side wall 13 and a shoulder portion 15 terminating in a neck 17 onto which is pressed and held firmly in place a blending fitting 19, preferably made of a synthetic organic polymeric plastic material, such as nylon or other suitable moldable and form-retaining polymer, preferably of the thermoplastic type. Blending fitting 19 includes a longitudinally extending tubular portion 21, the wall 22 of which is shown tapered and containing internal ribs 23.

Wall 22 determines a longitudinal passageway 25. A plurality (usually from 2 to 6 but even single passageways may be employed) of transverse passageways 27, located near the joinder of the shoulder and neck portions of the tube, passes through wall 22. The blending fitting includes an externally threaded outer portion 29 and a dispensing opening 31, which is a continuation of passageway 25. A sealing cap 33 may be screwed onto threaded portion 29 of the blending fitting to prevent unintentional discharge of contents from tube 11.

As is illustrated in FIG. 1, initially a first portion of dentifrice 35 is filled into the tube, as will be described with reference to FIG. 2, to the level or interface indicated by numeral 37. Then, an "insulating" or protective intermediate layer of extrudable non-reactive material 39 is applied so as to cover the exposed upper surface of the first dentifrice portion, following which operation the second portion of the dentifrice, identified by numeral 41, is filled into the tube while the tube is maintained in inverted position, as illustrated. Upon application of pressure to the end product streams of the first portion of the dentifrice pass through openings 27 into passageway 25, forming stripes or "inlays" in the surface of the dentifrice (the second portion) in such passageway. Entry of the first portion into the second portion is facilitated by the presence of the "upstream" ribs 23 and a uniform proportion of first dentifrice portion to second dentifrice portion is obtained. Because of the location of the transverse openings 27 near the discharge part of the container and the neck thereof, essentially all of the first portion of the product can be discharged and the dispensed product is of substantially uniform composition throughout dispensing. Ideally, the portion of dispensing passage 31 "downstream" (upon dispensing) of transverse openings 27 will be as short as is feasible so as to minimize contacting of any reactive portions of the dentifrice with each other during storage for any appreciable time between uses.

In FIG. 2 a plurality of tubes 11 is illustrated passing through stations under various filling and other mechanisms. Thus, at the first station (from the left) there is shown an empty tube, containing blending fitting and cap screwed onto it in sealing engagement, preparatory to filling. At such station the tube may be cleaned of minor particles of dust, etc. by an air blast. At the next station a first filling head 43 is illustrated, communicating with a source 45 of first dentifrice portion to be filled into a tube 11 in response to applied pressure. It will be noted that filling head 43 includes an internal passageway 47 which, in extension 47a, which forms an annular passageway, passes about the "upstream" end of blending fitting 19, when lowered, preventing any of the first portion of the dentifrice being filled from contacting the upstream end of the blending fitting or of entering passage 25 therein. Filling head 47 is lowered into position about blending fitting 19 and the desired proportion of the first dentifrice portion is inserted into tube 11 in a known manner, as filling head 47 is withdrawn, so that the "height" of the first dentifrice portion is at 37, as indicated. By such operation the entrapment of air is prevented and the upper surface of the first dentifrice portion, that nearest to contact with the second dentifrice portion, is minimized (compared to concentric filling, to be described later.

At the third stage of the filling operation, a highly preferred operation, a thin layer 39 of insulating, protective or buffering material, which very preferably is also extrudable, is introduced by a conventional filling head 49, as illustrated or by other suitable means, e.g., spraying means, gravity feed means or a pump, depending on the character of the protective material. For example, in some instances the protective material may be added to the tube or sprayed into place as a liquid or flowable substance and in other cases the filling head may be adapted to spread a thin layer of a thicker material over the "upper" (as illustrated) surface of the first dentifrice portion.

At the fourth stage filling head 51 is utilized to pressure feed the second dentifrice portion into tube 11 to the desired height thereof and at the fifth stage crimping means, not illustrated, crimp the upper end of the tube closed, as at 53. After sealing off of the container it is ready for cartoning, casing, warehousing and shipment.

Although the described product, with external "inlaid" dentifrice, as dispensed, usually by finger pressure application to the dispensing container, is completely satisfactory for many uses and may even be preferred sometimes, it may be preferable for the extruded dentifrice to be of a perfectly uniform surface appearance, not exhibiting any evidence of being composed of two different dentifrice portions. In such instances an insert of the type illustrated in FIG. 3 may be employed. The parts shown in FIG. 3 are the same as those of FIG. 1 except for the insert, which shall be described in detail. Insert 55 includes a tubular wall portion 57 defining passageway 59 through which second dentifrice portion 41 is fed by compression of tube 11. A transverse opening 61 or several such openings is/are so located as to allow the passage of the first portion of dentifrice through the wall and into the interior of the second dentifrice portion flowing through the discharge passageway. As will be seen from the figure, passageway 61 is angled as it passes through wall 57 so as to promote flow of the first dentifrice portion through it and the passageway is extended and turned in the direction of flow at 63 after passing through wall 57. To promote flow of the first dentifrice portion into the interior of the dispensing passageway 59 a tapered obstruction, shroud or similar structure 65 may diminish the volume of the second dentifrice portion flowing as it approaches the "outlet end" of part 63. Such shroud or baffle may be affixed to the interior of the wall 57 by any suitable means but preferably is molded into it or fused to it, as is the transverse passageway extension 63.

The material of construction of the tube is preferably aluminum with a polymeric plastic cap and blending fitting. The dentifrice and the different portions thereof, the various compositions of which will be described later, will normally be readily extrudable through the dispensing opening, which will often be 0.4 to 1 cm. in diameter and the dentifrice dispensed will be form retaining, i.e., will not flow or readily pass through the bristles of a toothbrush on which it is deposited. Because of such characteristic of the final dentifrice and its component portions and because of the presence of the separator between them the two reactive dentifrice portions packaged in the dispensing tube or other suitable container will not tend to intermix after packaging. The openings in the dispensing passage wall through which the first dentifrice portion passes usually are of a diameter from one to four millimeters, which diameter will normally be from 0.1 to 0.5 times that of the dispensing passageway. Of course, instead of circular openings openings of other shapes, e.g., triangles, ellipses, arcs, segments and rectangles, may also be employed but the cross-sectional areas thereof will usually be equivalent to those previously given for circles of the diameters mentioned.

The number of openings through the dispensing passageway walls and the sizes thereof will be chosen to regulate the desired proportions of the dentifrices to be discharged. The openings will preferably be located nearer to the dispensing end of the tube wherein the first dentifrice portion is stored before dispensing. Normally such location will be at the end of such storage zone, external to the discharge passageway or no more than one centimeter, preferably no more than five mm. from it. Similarly, the distance from the transverse passageway exit, where the first dentifrice portion contacts the second dentifrice portion, to the end of the dispensing passageway where dentifrice may lie between uses (to where the toothbrush removes it), will be kept small, preferably being no more than one cm., more preferably being less than 5 mm.

The first dentifrice portion, in the containers of FIGS. 1-3, will usually have an "upper" surface thereof no closer to the inlet opening of the main discharge passageway than about 1 cm. and preferably no more than 5 mm. Such a range of distances may be from 0.3 to 2 cm. and preferably is from 5 mm. to 1 cm. The extrudable separating or buffer layer of protective material between the first and the second dentifrice portions will normally be no thicker than 3 mm. and preferably is 1 to 2 mm. thick but may be thicker in some special cases, e.g., 1 to 6 mm.

Instead of employing blending fittings of the type shown on collapsible metal tubes, as illustrated, such fittings may also be used with resilient polyethylene tubes, "aerosol" pressurized gas propelled dentifrice outlet valves, squeeze bottle outlets and with other pressure actuated dispensers. It will be evident to one of skill in the art how various blending fittings may be adapted for installation in such other containers.

Although it is desirable to have a buffer layer of non-reactive material between the first and the second dentifrice portions, in some embodiments of the invention, due to the limited area of the interface between such portions, little reaction will occur and therefore the absence of the buffer may be acceptable, although the resulting product is not preferred for best stability of the dentifrice. Normally, as in the illustrated embodiments of the invention, the unitless ratio of the interface area to the dentifrice volume in the filled dispensing container will be less than 0.3, preferably less than 0.2, e.g., 0.05 to 0.2. Nevertheless, in some aspects of the invention one may employ "mixed" dentifrices such as those made by the methods of U.S. Pat. No. 3,881,529 and British Pat. No. 962,757, both incorporated herein by reference, without intervening buffer layers. Of course, when the filling machines of such patents are modified to allow the interposition of a buffer between the layers of dentifrice, lesser interaction will be obtained. Also, when using such dentifrices no special blending fitting is necessary in the dispenser neck.

In FIGS. 4 and 5 there is shown another modification of the present invention wherein the dispensing container of dentifrice 71 includes first and second dentifrice portions 87 and 91 in tube 73 with separator 89 between them. Instead of employing particular blending means, such as is shown in FIGS. 1-3, the dentifrice components and the separator are filled into the tube in such manner that they may be extruded from it together, providing a desired blending of dentifrice portions containing the reactive components, which are prevented from undergoing premature reaction by separation, most preferably by the presence of the intervening separator.

Dentifrice tube 73, into which the dentifrice composition, including separator, has been filled, is shown as substantially cylindrical (but other shapes can also be used), with cylindrical wall 75, shoulder 77 and neck 79. About the neck of the tube is illustrated, somewhat schematically, externally threaded collar 81, onto which sealing cap 83, with intermediate gasket 85 inside, may be screwed. The bottom of the tube (the tube is shown inverted in FIG. 4) is crimped at 86 to seal it.

FIGS. 4 and 5 illustrate an embodiment of the present invention capable of maintaining reactive portions of dentifrice (containing reactive components) separate during storage but allowing dispensing thereof for use by finger pressure deformation of collapsible tube 73. As shown, the first portion of the dentifrice, a minor proportion compared to the second portion thereof, is located adjacent to the wall of the dispensing tube 75 and the second portion, the major proportion of the dentifrice, is located interiorly thereof, with a barrier separator of gel or dentifrice devoid of reactive components between them. In the embodiment shown the thickness of the first portion in the neck near the outlet from the tube is illustrated somewhat schematically (to show the flow path) and as it will sometimes be immediately after filling and before use of the dentifrice has been begun. Thus, initially a greater proportion of the first dentifrice portion may be discharged from the dispensing container due to relatively even disposition of a circumferential deposit of the first portion about the walls of the container. However, in the event that such increased concentration of the first portion material is considered to be undesirable or objectionable for any reason, filling methods employed may be modified, as will be described in reference to FIG. 6, so as to diminish the thickness of the first portion in the neck and shoulder sections of the dispensing tube. In any event, it will be clear that after the first few uses of the dentifrice pressure on walls 75 of tube 73 will cause the dispensing together in desired proportions of both portions of the dentifrice and the extrudable separator. When reaction between the two components is desirable, some of it may take place after dispensing but most of it will occur when the dentifrice is employed in brushing of the teeth. Similarly, although when reactive components that are desirably maintained separate and are not intended for reaction before or during use are utilized some reaction may occur during brushing of the teeth but in such cases appreciable desired effects of the individual components and not the reaction products are also obtainable. For example, although dicalcium phosphate may react somewhat with sodium fluoride or sodium monofluorophosphate in the mouth, a substantial proportion of the fluorine-containing compound will be available to be absorbed by the teeth and to harden tooth enamel and the dicalcium phosphate will still be able to effect its desired polishing function.

An important property of the present composition is the maintenance apart of reactive compounds in the dentifrice portions during storage before use. Such storage period may in some cases amount to as much as a year before use and the dentifrice in the tube may be consumed within a period normally ranging from about a week to about a month. Thus, for comparatively slow reactions, even if in the period of storage in the tube during use some of the reactive components are mixed together, providing that most of such are not the utility of the invention in preventing such reaction during the much longer storage period is evident. However, careful dispensing of the dentifrice allows for substantial maintenance apart of the reactive dentifrice portions, with the separator between them. Utilization of one of the known mechanical devices for attachment to a toothpaste tube for evenly discharging its contents, as by rolling the tube about a cylinder initially affixed to the crimped end thereof, helps to prevent any premature mixing of the dentifrice portions. Also, even manual dispensing of the contents permits the desired even and proportional discharge of separate reactive proportions because such portions will be of similar rheological properties (ideally they are of the same viscosity, which can be adjusted by varying the concentration of gelling agent or other component). Because the various portion and separator compositions flow similarly they will move toward the dispensing outlet of the dentifrice tube together in substantially "laminar" flow and will not unduly intermix, even when dispensed in a "careless" fashion.

In the embodiment illustrated in FIGS. 4 and 5 (also shown in FIG. 6) the first (minor) portion of the dentifrice is circumferentially positioned but it is within the invention to have it centrally or axially positioned too and in some instances variations thereof may be desirable. Thus, the first portion, separated from the second portion by the extrudable separator, may be in the form of stripes about the circumference of the second portion or may be located in a plurality of cores within said second portion so as to provide particular appearances or taste sensations (with coloring or stronger flavoring being in the stripes or cores) and in some cases to assist in promoting more uniform discharge of the product. However, it is preferable to have the portions of the dentifrice concentrically positioned with respect to each other. Such a structure comparatively simplifies filling and avoids the use of more complex filling apparatuses.

In FIG. 6 is shown a method for filling dentifrice tube 73 with first and second portions of dentifrice of this invention, concentrically positioned and separated. Tube 73, inverted, capped with cap 83 and uncrimped, is passed or placed under filling head 95 with which a source 93, not shown in detail, of a first portion of a dentifrice to be filled into the tube is connected. The filling head is inserted into the tube and the first portion of dentifrice is discharged into the tube, passing through passageway 97 and transversely directed passageways 99 as the tube is raised, so as to deposit a substantially even coating thereof 101 on the interior wall of the tube. (For clarity of presentation the materials being filled are not shown in the filling heads of FIGS.' 2 and 6. Also a source 105 of separating material 103, communicating with filling head 107, allows flow through passageways 113 and 109 of the separating material into the tube and from source 117 of second dentifrice portion 115 that material is added to the tube through filling head 119 and passageway 121 thereof. Then the tube is crimped at 86 and the finished product 71 is packed and sent to storage, preliminary to shipping, sale and end use.

To facilitate even application of the first dentifrice portion of the body, shoulder and neck portions of the tube interior, the nozzles or discharge passageways at the tube bottom may be modified, with some being directed into the neck, some toward the shoulder and others against the cylindrical wall so as to deposit the desired thicknesses of first dentifrice portion thereon. Mechanisms may be employed to terminate discharge of the dentifrice through the neck and shoulder orifices before or early during the withdrawal of the filling head. To prevent or minimize flow of the first dentifrice portion downwardly, tube 73 may be cooled prior to filling so as to congeal the dentifrice and hold it to the wall where applied. Additionally, the tube may be rotated during filling (as may be the filling head), utilizing centrifugal force to hold (and apply) the dentifrice portion to the wall of the tube. Similar modifications of the apparatus may be made for application of the barrier material 103. Alternatively, the indicated designs or designs similar to them may be utilized to apply the first dentifrice portion to the tube wall only or primarily, allowing some thereof to flow into the shoulder and neck portions of the tube, and such operation may also be practiced with respect to the application of the extrudable separator.

Various other filling methods may also be utilized, including preliminary molding (possibly with "freezing") of the "assembled" dentifrice and insertion into the tube, which will be vented during a portion of the addition so as to prevent air entrapment. More complex filling heads may be utilized wherein the plurality of dentifrice portions and separator are simultaneously added to the dentifrice tube in desired locations. Also, the major portion of the dentifrice may be applied to the inner circumference of the tube, with the minor proportion being applied internally thereof, with the separator between them. Such filling may be effected using the filling head schematically illustrated (although the discharge ports 109 of filling nozzle 107 will be shortened) or by apparatuses like those just described for simultaneous additions of the various dentifrice portions. Of course, apparatuses like those of the U.S. and British patents previously mentioned may also be modified for use in filling dentifrice tubes with the present compositions. Although not illustrated, it is also within the invention to utilize the described methods for the filling of "pressurized aerosol" cans, resilient squeeze bottles and other dispensing containers.

The dentifrices produced by the dispensing of both chemically reactive portions thereof from a container in which they are maintained substantially separate will be extruded or otherwise discharged from the container as a unitary form-retaining ribbon, of sufficient viscosity or thickness to rest atop normal toothbrush bristles without descending between them. The dentifrice produced on the component portions may be opaque, translucent or transparent or may be mixtures thereof but usually preferably will appear to be of a single color and type. Preferably also, only two dentifrice compositions are fused or extruded together but more can be used. For example, a major or second dentifrice portion, such as that identified by numeral 41 in FIG. 1, may be composed of different compositions, each of which may be a longitudinal "block" in the tube, parallel to but separate from other such compositions. Similarly, the minor or first dentifrice portion may be composed of a plurality of different component dentifrice compositions separated from each other. If desired, portions of the dentifrice may include encapsulated materials, especially encapsulated materials which are most chemically reactive with other components of the dentifrice.

Dentifrice compositions normally comprise a vehicle, a polishing agent, a gelling agent and a surface active or detersive agent. Generally, the vehicle is compatible with all other dentifrice constituents although, as when it is aqueous, it may promote reaction between other normally chemically reactive components. However, the polishing agent, which may contain or may produce insolubilizing ions, such as calcium ions, which can react with soluble fluorides to insolubilize them and thereby inactivate them, and detergents, such as anionic detergents, which can react with cationic antibacterial compounds to inactivate them, should be separated from such reactive materials, when possible, to prevent loss of desired effect during manufacture and storage. The usual vehicles of dentifrices are water and lower polyhydric alcohols of 3 to 6 hydroxyl groups and 3 to 6 carbon atoms per molecule. The most preferred humectant vehicles are glycerol and sorbitol, usually in an aqueous medium. Most preferably aqueous glycerol-sorbitol mixtures are employed. When transparent dentifrices are manufactured, with the index of refraction of the polishing agent being approximately the same as that of the vehicle, the proportion of moisture is usually held to a minimum. Instead of the particular polyhydric alcohols previously mentioned other liquid polyols may also be utilized, such as polyethylene glycols, mannitol and other sugar alcohols, and polyoxyethylene alcohols.

The polishing agents are finely divided water insoluble powdered materials of particle sizes such that they pass a 140 mesh screen, U.S. Standard Sieve series and preferably are from 1 to 40 microns in diameter, most preferably 2 to 20 microns, with distributions of particle sizes being normal over such ranges. Examples of such agents are dicalcium phosphate, tricalcium phosphate, insoluble sodium metaphosphate, crystalline silica, colloidal silica, complex aluminosilicates, aluminum hydroxide (including alumina trihydrate), magnesium phosphate, magnesium carbonate, calcium carbonate, calcium pyrophosphate, bentonite, talc, calcium silicate, calcium aluminate, aluminum oxide, aluminum silicate and silica xerogels, all of which have polishing activity but are not objectionably abrasive. With respect to many such compounds the corresponding alkali metal or alkaline earth metal salts are also useful and may be employed, providing that they are sufficiently insoluble. Most of the polishing agents mentioned are most useful in the preparation of opaque dentifrices, but some them, such as the colloidal silicas, especially silica xerogels, and complex sodium aluminosilicates, may be used to make clear dentifrices because their indexes of refraction approximate those of the rest of the dentifrice constituents in an appropriate vehicle.

The gelling agents used to make the dentifrices of the present invention are known in the art and include the natural and synthetic gums and gum-like materials, such as alkali metal carboxymethyl cellulose, hydroxyethyl carboxymethyl cellulose, polyvinyl pyrrolidone, Irish moss, gum tragacanth, hydroxypropyl methyl cellulose, methyl cellulose, starches, starch glycolates, polyvinyl alcohol, alginates, carob bean gums, the hydrophilic colloidal carboxyvinyl polymers, such as those sold under the trademarks Carbopol 934 and Carbopol 940, diatomaceous earths, bentonite and other natural clays (these also may function as polishing agents), proteinaceous materials, either animal- or vegetable-derived, and silicated clays sold under the trademarks Laponite CP and Laponite SP. Certain colloidal silicas such as the aerogels, Syloids 244 and 266 and Aerosil, and pyrogenic silicas, such as those sold as Cab-O-Sils, may also be used for thickening or gelling properties. Of course, as with the other constituents of the dentifrices, mixtures thereof may be employed to obtain specially desirable properties in the product. Generally, the gelling materials utilized are gellable with water or alkanols, especially with polyhydric alcohols, such as glycerol and sorbitol. Usually the gel is formed with at least some water present.

The synthetic organic detergents or surface active agents which may be employed in the present compositions assist in emulsifying or otherwise dispersing the components of the dentifrice uniformly and add their cleaning action to the product. In some cases they are germicidal and aid in prophylaxis. Although the organic surface active materials used may be anionic, nonionic, ampholytic or cationic, it is generally preferred to employ, at least as the major detersive constituent, either an anionic or a nonionic material, or a mixture thereof, and of these the anionics are highly superior in most compositions. In addition to their desired surface active, emulsifying and detersive effects, such materials impart to dentifrices good foaming properties. Generally, they will include long chain fatty or poly-lower alkoxy groups plus hydrophilic radicals. Usually, the anionic detergents will be in the forms of salts, especially water soluble salts of alkali or alkaline earth metals, with those of the alkali metals being strongly preferred, especially in the present "fluoride" dentifrices where interactions with the fluorine containing hardening agent should be presented. Among the useful anionic detergent materials may be mentioned the higher fatty acid monoglyceride monosulfates, such as the sodium salts of the monosulfates of monoglycerides of hydrogenated coconut oil fatty acids, higher alkyl sulfates, such as sodium lauryl sulfates, alkyl aryl sulfonates, such as sodium linear dodecyl benzene sulfonate, olefin sulfonates, such as sodium higher olefin sulfonate in which the olefin group is of 12 to 20 carbon atoms, higher alkyl sulfoacetates, higher fatty acid esters of 1,2-dihydroxy propane sulfonates, the substantially saturated higher aliphatic acyl amides of lower aliphatic aminocarboxylic acid compounds, such as those having 12 to 16 carbon atoms in the fatty acid, alkyl or acyl radicals, higher alkyl poly-lower alkoxy (of 10 to 100 alkoxies) sulfates, higher fatty acid soaps and the like. In this specification for convenience and ease of presentation, the soluble (usually alkali metal) soaps are considered to be synthetic organic detergents. Examples of the mentioned amides are N-lauroyl sarcosine and the sodium, potassium and ethanolamine salts of N-lauroyl-, N-myristoyl- and N-palmitoyl sarcosine. In the above descriptions, "higher" refers to chain lengths of 12 to 20 or 22 carbon atoms, preferably 12 to 18 carbon atoms and most preferably 12 to 16 carbon atoms. Of course, in broader embodiments of the invention various other sulfuric reaction products which include long chain hydrophobic groups and hydrophilic radicals are also useful and such compounds are well known. See the text *Surface Active Agents,* Vol. II (1958), by Schwartz, Perry and Berch.

Among the nonionic materials which have been found to be useful detergents are those including chains of lower alkylene oxides, e.g., ethylene oxide, propylene oxide, in which there are present from 10 to 100 or more moles of lower alkylene oxide. Among such materials are the block co-polymers of ethylene oxide, propylene oxide and propylene glycol, sold as Pluronics, the alkyl phenyl polyethoxy ethanols, sold as Igepals, the mixed copolymers of ethylene oxide and propylene oxide, sold as Ucons, and various other well known nonionics derived from fatty alcohols or acids and polyethylene oxide. The amphoteric agents and cationics, which may sometimes be present, although usually it will be desirable to avoid the presence of cationic detergents together with anionic materials, include quaternized imidazole derivatives, sold as "Miranols, such as Miranol C₂M", and cationic germicides, such as diisobutylphenoxyethoxyethyl ammonium chloride and tertiary amines having a higher fatty alkyl group and two polyoxyethylene groups attached to the nitrogen thereof.

In addition to the mentioned materials various additionally active components and adjuvants may also be present for their desired effects. Among the most important of these are fluorine-containing compounds which are often present for their desirable activity in hardening tooth enamel, thereby helping to inhibit tooth decay. Antibacterial compounds, astringents, protein precipitating agents, flavors, colors and effervescing components may also be present. The fluoride compounds most preferably employed include sodium monofluorphosphate, sodium fluoride and stannous fluoride. Of these, the more soluble sodium salts are most liable to be inactivated by reaction with alkaline earth metal salts and therefore are preferably maintained separate from such salts in the dentifrice composition. For example, in a fluoride dentifrice packed in a dispensing container in accordance with this invention the formulation will be divided into two parts, substantially all of the ingredients except any chemicals reactive with the fluoride e.g., dicalcium phosphate, tricalcium phosphate, calcium carbonate and any other similarly or more soluble calcium salts, being concentrated in one of the separate compositions while said calcium-containing compound(s) is/are in the other with the other dentifrice constituents, each such composition part having none of the other chemically reactive component present. When a cationic bactericide such as a quaternary ammonium bactericide is present in the composition, if it is desired to employ an anionic detergent the cationic and anionic surface active materials will be maintained in the separate portions of the dentifrice, which portions are blended together upon dispensing. The quaternary ammonium salts are those in which the anion is usually halogen or sulfate, one or two substituents on the nitrogen are higher alkyl of 10 to 18 carbon atoms and the other substituents are lower alkyl of 1 to 4 carbon atoms or aryl, e.g., phenyl. Among such compounds are cetyltrimethyl ammonium bromide, dibenzyl dimethyl ammonium chloride and benzyl dimethyl stearyl ammonium chloride. If desired, so that the portion containing the cationic compound will have an effective surface active agent present therein, a nonionic surface active agent may be utilized in it. Similarly, to give body to the portion of the dentifrice containing fluoride or fluorine-containing compound a polishing agent may be present with it that is non-reactive with the fluorine, e.g., silica. Similar considerations govern the use of protein precipitating agents which may be kept separate from proteinaceous gelling materials and other protein-containing compounds in the dentifrice. Also, if effervescent dentifrices are to be made one portion of the effervescent mixture may be kept in each of the dentifrice parts, e.g., sodium bicarbonate in one part and food acid or food acid precursor, e.g., gluconodelta-lactone, in the other part. Such food acid, e.g., citric acid, gluconic acid, malic acid, tartaric acid, may also be used to change the pH of the dentifrice in the mouth as brushing is continued and in some cases it will be desirable to have at least a portion of the acid encapsulated to further promote later acidification during the toothbrushing operation. Of course, other chemically reactive or chemically incompatible pairs of constituents may also be employed, providing that they are separated in accordance with this invention.

Among the flavoring materials employed, in addition to sweetening agents, such as saccharin, are the essential oils but also included are various flavoring aldehydes, esters, alcohols and similar materials known in the art. Examples of the essential oils include those of spearmint, peppermint, wintergreen, sassafras, clove, sage, eucalyptus, lemon and lime. Also useful is methyl salicylate.

The proportions of the various dentifrice components are those normally employed in the manufacture of dentifrices and the specifications for the components are essentially the same. Thus, such materials are described in the textbook, *Cosmetics:Science and Technology*, by Sagarin, Second Printing, 1963, published by Interscience Publishers Inc., hereby incorporated by reference. In the manufacture of the usual opaque dental creams there will normally be present 20 to 75% of polishing agent whereas in the manufacture of clear dental gels this percentage may typically be from 5 to 40%. The preferred proportions of such constituents are 40 to 60% and 10 to 30%, respectively. Gelling agent contents will usually be less than 5% and in most instances from 0.1 to 3% will suffice, with a preferred range, especially applicable when sodium carboxymethyl cellulose is the gelling agent, being from 0.3 to 1.5%. The dentifrice vehicle, exclusive of water (some of the water excluded is that normally present with sorbitol), will normally be from 10 l to 85% of the product, with from 10 to 35% being a typical range for the production of opaque dentifrices and from 40 to 85% being useful for the manufacture of clear dental preparations. Preferred ranges are, respectively, from 15 to 30% and 50 to 75% but intermediate ranges may be preferred too in some cases. Polyhydric alcohols are usualy preferred as the vehicles, preferably with water. In the most preferred vehicles, in which glycerol is mixed with sorbitol, the glycerol:sorbitol ratio will usually be from 0.3:1 to 10:1 for the opaque products and from 1:5 to 5:1, more preferably 1:3 to 1:1 for the clear dentifrices. Moisture contents of the dentifrices, including moisture normally present in the sorbitol solution employed, will generally range from 5to 35%, usually being 8 to 30% and preferably 20 to 30% of the opaque dentifrices. For clear dentifrices this range may be from 0 to 30%, preferably 10 to 20% and more preferably 15 to 30%. Surface active agent or detergent content will usually be from 0.5 to 5% of the dentifrice but may be increased to 10% in some instances. In preferred embodiments of the invention the detergent content will be from 1 to 3%. When nonionic detergents are employed their content will normally not be outside the range of 0.1 to 3% and will preferably be from 0.5 to 2%. Adjuvants, exclusive of flavorings and solvents, will normaily be from 0.1 to 10%, preferably being from 0.2 to 5%. Flavoring will generally constitute from 0.5 to 2.5 percent of the dentifrice and solvent content may be 0 to 10% and, if present, is preferably 1 to 5%, e.g., 2% of chloroform or equivalent. The adjuvants include tooth treating (hardening) chemicals such as fluorides; anti-bacterial agents; components of effervescing reaction mixtures; protein precipitation agents; pH regulators; and astringents. Such materials and other adjuvants, such as coloring and whitening agents, preservatives, silicones, chlorophylls, ammoniated compounds, lubricants, etc., are described in detail in U.S. Pat. No. 3,840,657 (Norfleet), as are other dentifrice components and formulations. Said patent is hereby incorporated by reference.

The dentifrice component parts may be made by standard manufacturing methods before being filled into the dispensing containers by any of the techniques previously described. Thus, as in U.S. Pat. Nos. 3,711,604 and 3,840,657, the dentifrice may be degassed during manufacture or gas bubbles may be intentionally added to it.

When two separate dentifrice portions are employed, each containing a component reactable with the other separate component of the composition, one portion, designated the first portion, may comprise from 2 to 50% of the dentifrice and a second portion may be from 98 to 50% thereof (excluding in such calculations any intervening separating dentifrice or other materials such as a gel made from a dentifrice binder, vehicle and water). Preferably such ranges will be from 5 to 20% and 95 to 80%. The intervening material may be a gel as described or may be a complete dentifrice except for the two reactive components. The proportion thereof will usually be from 0.5 to 5% of the dentifrice, by weight. Including the gel as part of the dentifrice (and it should be so included because it is extruded with the initially separated dentifrice portions in one aspect of the invention throughout dispensing and in the other at the completion of dispensing), the ranges of percentages are 2 to 49.5%, 50 to 97.5% and 0.5 to 10%, preferably 5 to 19%, 80 to 94% and 1 to 5%, respectively. More preferably the ranges are 8 to 15%, 82 to 90% and 2 to 3%, respectively.

The compositions of the separate dentifrice portions will be modified in each case according to the final formulation desired. Thus, when a soluble fluoride, such as sodium fluoride or sodium monofluorophospate or a mixture thereof is present in a percentage which will normally be from 0.02 to 3%, preferably 0.3 to 2%, it will be in a portion of the dentifrice, preferably the first portion thereof, without any reactive insolubilizing material being present therein, such as dicalcium phosphae or other reactive alkaline earth metal salt. Similarly, when an astringent salt is present, such as aluminum chloride or zinc sulfate, these will be maintained separate from fluorine-containing compounds and anionic detergents. Cationic antibacterials and various other antibacterial compounds will be kept separate from reactive materials, such as anionic detergents. Protein precipitating agents, such as aluminum salts, will be separated from proteinaceous binders. Acids and bases will be maintained apart. Materials that react to produce a gas, such a carbon dioxide, will be kept separate from each other until they are mixed on dispensing. The proportions of antibacterial compound, astringent, protein precipitant, acid (or base) and effervescing "mixture" will usually be in the range of 0.1 to 2%, 0.2 to 1%, 0.1 to 1%, 0.2 to 2% and 0.3 to 3%, respectively. Of course, various mixtures of such materials may be employed too but care should be exercised that all inter-reactive materials are maintained separate until final mixing or shortly before.

The modifications of the separate dentifrice formulas to be kept apart in the dispensing container before actual dispensing may cause the omissions of a particular desirable component from one of the portions but it is within the invention to substitute a component having a similar effect but not being objectionably reactive. Thus, silica may be used as a polishing agent or bodying agent in place of a calcium salt in the component containing fluoride tooth hardening agent and nonionic surface active agent may be employed with the cationic antibacterial compound instead of the usual anoinic detergent. Of course, when an acidifying agent such as citric acid is employed, in addition to being kept separate from sodium bicarbonate or other suitable compound with which it reacts to produce the desired foaming on dispensing, it should be maintained separate from other alkaline materials or compounds with which it might also react, such as calcium carbonate. The sodium bicarbonate may be employed in dentifrice formulations in proportions in excess of the stoichiometric proportions required to produce carbon dioxide bubbles, with the excess being useful as an auxiliary polishing agent and breath sweetener.

The following examples illustrate the invention but should not be considered as limiting it. Unless otherwise mentioned, all parts are by weight and temperatures are in °C.

EXAMPLE 1

|  | Percent |
| --- | --- |
| Glycerol | 4.5 |
| Sorbitol | 17.5 |
| Sodium carboxymethyl cellulose (7MF, Hercules) | 0.8 |
| Sodium benzoate | 0.5 |
| Sodium saccharin | 0.2 |
| Water | 22.4 |
| Dicalcium phosphate (90% hydrate) | 45.5 |
| Fumed silica (Cab-O-Sil M5) | 5.0 |
| Sodium lauryl sulfate | 1.5 |
| Sodium fluoride | 0.5 |
| Sodium monofluorophosphate | 1.0 |
| Peppermint flavor | 0.6 |
|  | 100.0 |

The above final formula dentifrice is obtained by making two separate dentifrice compositions in accordance with the present invention and filling them into a dispensing tube of the type shown in FIG. 1 by the method illustrated in FIG. 2. The first composition filled comprises about 12% of the entire formula, including 1/10 of the percentages of each of the constituents except the dicalcium phosphate, of which none is present, and includes the entire percentages of silica and the fluorine-containing tooth hardening compounds. Next, the second portion of the dentifrice is added, with no separating material between the "layers", which take the positions shown in FIG. 2. The tubes are crimped at the upper ends thereof (really the bottom seals), having been previously (before filling) sealed tight at the cap ends. After storage for six months under normal storage conditions, when the mixed dentifrice is dispensed from the tubes in accordance with the present invention the active content of fluorine-containing hardening agent is significantly greater than that from a control formula wherein the various components are homogeneously mixed together before filling, stored for the same time in a conventional collapsible dentifrice tube and dispensed from such tube.

In an improvement of the above product the percentages of the various components and dentifrice portions are reduced to 98% thereof and a gel layer, as illustrated in FIG. 2, is placed atop the first (minor) dentifrice portion to separate it from the second portion. The gel layer constitutes 2% of the final dentifrice product and is composed of 5% of sodium carboxymethyl cellulose in 95% of a glycerol - sorbitol - water mix like that in the 98% of the dentifrice. The gel is cler but may be whitened to resemble the dentifrice portions by inclusion therein of some, e.g., 1/10, of the 5% of Cab-O-Sil M-5 of the formula. With the gel separator in place as described the first and second dentifrice portions at the interface show little interaction, compared to the interface of the prior described product of this example and consequently the activity of the tooth hardening fluoride components is increased. In a further modification of the described product the fitment illustrated in FIG. 3 is employed, so that the first portion of dentifrice, rather than forming "invisible stripes" about the circumference of the extruded major dentifrice portion, is extruded through the middle of such portion, where it is even less visible. Such is done with the desribed compositions with and without intervening extrudable "insulating" layers between the dentifrice portions. Of course, since the storage conditions for such product are essentially the same as those of the products previously described, the fluorine compound stabilities are essentially the same, too.

In still another modification of this example instead of employing the sodium carboxymethyl cellulose gel intermediate the two dentifrice portions in the collapsible dispensing tube, 2% of dentifrice formula containing no dicalcium phosphate (silica is substituted for it) and containing no fluorine-containing compounds is employed as the separating agent. The stabilities of the fluorine-containing compounds in the final dentifrice are thereby preserved better than in homogeneous products. Similarly, in other dentifrices desirably including reactive components this same procedure may be followed, with a separator being employed which is of the composition of the product less the reactive material (or of essentially such composition).

In all the experiments described the sizes of the dispensing orifices and the fitment orifices and the numbers of such fitment orifices are controlled so that a constant composition of product will be dispensed and both portions thereof will be consumed proportionately, maintaining the final dentifrice composition substantially constant during its entire use. Thus, to effect this with 12% of the minor component and 88% of the major component of the dentifrice, neglecting the presence of any separating composition, one may employ a tube outlet having a diameter of about 0.8 cm. and a fitment having six openings, each of 0.1 mm. Of course, allowances will be made in the choices of orifices to compensate for different viscosities of the dentifrice components. Also, the various other tube characteristics, proportions and other conditions are those described in the specification, with the averages of the preferred ranges being used.

EXAMPLE 2

The formulation of Example 1 is modified to include a 50:50 mixture of glycerol and sorbitol in place of the 20:80 mix, Irish moss in place of sodium CMC, a mixture of hydrated dicalcium phosphate and tricalcium phosphate (50:50) in place of the dicalcium phospate (90% hydrate), sodium N-lauroyl sarcosinate in place of sodium lauryl sulfate and sodium monofluorophosphate in place of sodium fluoride. Different flavors are employed in place of peppermint flavor, e.g., spearmint, clove. The products resulting are of essentially the same tooth hardening characteristics as those of Example 1, after a comparable storage period. They may be made by similar methods, conveniently at room temperature, using automatic filling equipment such as that illustrated in FIG. 2.

EXAMPLE 3

The products of Examples 1 and 2 are made by the method of U.S. Pat. No. 3,881,529 so that the dentifrice parts are separately located in the dispensing tube during storage but are longitudinally situated, as in a plurality of stripes in a matrix or a body of the major proportion of the material. Such product is not as stable on storage as those previously described but is more stable than a homogeneous product including the same components. When the separator of extrudable gel or dentifrice composition not containing either of the reactive components is employed between the stripes and the major dentifrice portions stability is increased further.

EXAMPLE 4

The formulas of Examples 1-3 are modified to include in the minor portion 0.4% of cetyltrimethyl ammonium bromide, together with all the dentifrice constituents except the anionic detergent, and the sodium fluoride and sodium monofluorophosphate are omitted. In place of the sodium lauryl sulfate, 1.3% of which is present in the major portion of the dentifrice, 0.2% of nonionic detergent (polyoxyethanol, Neodol 45-11) is used in the minor portion. The proportion of vehicle is increased therein to compensate for the absence of the fluorine compounds. After six months storage of the products made the stability of the quaternary germicide is greater than it is in homogeneous products of the same formula. As in the other examples, when an extrudable gel separator, such as that of Example 1 or a separator of the dentifrice composition less reactive components, such as that of Example 3, is employed "interface" stability and overall product stability are improved more.

EXAMPLE 5

Examples 1-3 are repeated with 1.5% of citric acid replacing the fluoride and monofluorophosphate and despite storage for six months the acidification effects of the acid are apparent on use. On the other hand, in a control composition the acid is almost entirely consumed in neutralizing the dicalcium phosphate, converting a substantial proportion to monocalcium phosphate, on storage. Similar effects are obtained when other food acids, such as tartaric and malic acid, are employed, instead of citric acid, and when other "alkaline" polishing agent salts are used. With separators like those of the previous examples being used even greater stability of the dentifrice is obtained.

EXAMPLE 6

The experiments of Examples 1-3 are repeated with an effervescent "mixture" being employed, 1% (on a total product basis) of sodium bicarbonate being with the major portion of the dentifrice and 1% (same basis) of citric acid being with the minor portion, again with the fluorine-containing compounds being omitted. The product expands on dispensing, due to reaction of the two components, despite storage for six months. A control homogeneous product reacts prematurely and causes undesirable swelling of the container and excessive speed of dispensing when the container cap is removed. Even better stability on storage is obtainable by utilizing a separator between the dentifrice portions, as was previously described.

In a like manner protein precipitating compounds are included in the formulations, being kept separate from any proteinaceous gelling materials with which they might be reacted.

The products made, as described in the above examples, are all opaque white and exhibit no tell-tale stripes. They are readily manufactured and after lengthy storage periods are still active. However, if desired, colorants may also be employed by including them in one or the other or both portions of the composition to be dispensed. Also, when desired, clear dentifrices are made by following the procedures of the above examples but substituting for the initial dentifrice base composition compositions of Examples 1 and 2 of U.S. Pat. No. 3,840,657. In such cases, the difference between the two "phases" may be minimized or may be accentuated by using transparent coloring materials, too. Of course, in transparent dental gels different polishing agents are employed and opaque constituents are avoided. Thus, it is a decided advantage of the present invention that the separating composition is usually clear so that it does not make its presence evident in transparent dentifrices nor in opaque compositions. Such advantage is even more significant in relation to products in which the separator is continuously discharged with the dentifrice, which will be described in more detail in the following examples.

EXAMPLE 7

The experiments of Examples 1-6 are repeated with dispensing of the dentifrice being from a pressurized dispenser commonly referred to as an aerosol can, pressurized with nitrogen at 3, 5 and 10 kg./sq. cm. The dispensed product, released upon depressing of a dispensing spout, which depresses a valve stem and opens a passageway for dispensing, has the properties of the tube-dispensed products previously described. Before pressurizing, the container may also be filled by either the method illustrated in FIG. 2 hereof or that of U.S. Pat. No. 3,881,529. The pressurized container, as described, should be held inverted, with the dispensing valve at the bottom thereof. However, it is within this invention to employ a dip tube, as is well known in the art, so that dispensing at the container top may be obtained but this is often avoided due to possible reaction of the components in the tube after mixing and before dispensing. However, the tube design can be modified, preferably by making it thinner, for use thereof under some circumstances.

EXAMPLE 8

The compositions of Example 1 are employed and are filled into dentifrice tubes in the manner illustrated in FIG. 6, with the first composition, comprising 12% of the entire formula, being applied to the inner body, shoulder and neck walls of the tube first, followed by the barrier or separator layer, which is 2% of the total contents of the tube, and the second portion, which comprises the balance of the tube contents. The first dentifrice portion, which like the other portion and the separator, is of sufficient viscosity and other rheological properties at room temperature (25° C.) so as to retain its shape atop the bristles of a toothbrush, is directed against the wall portion of the tube from the filling head passageway with sufficient velocity so that it adheres to the wall while the tube is being filled with separating material and the second dentifrice portion. However, should any downward flow or dripping of the first dentifrice portion be considered to be excessive, the tube may be cooled, for example, to a temperature of 5° C., so as to help to congeal the dentifrice layer thereon and hold it in place during subsequent filling operations. Metal tubes, especially aluminum tubes, are of good heat transfer characteristics and may be so cooled prior to addition of dentifrice or during such addition. Alternatively, a cold air blast may be directed onto the interior as well as the exterior parts of the partially filled tube (including the filled product) so as to further congeal and additionally help to fix in position the first dentifrice portion. The dispensing heads utilized are preferably those wherein material to be filled is directed substantially uniformly in all directions about the dispensing head axis but the head may be rotated to facilitate such distribution and/or the tube may be rotated during filling of the first dentifrice portion and the separator. The last method additionally helps to hold the dentifrice in place on the tube wall. Filling with the second dentifrice portion may be as described in Example 1 and in the preceding specification, with no special steps being necessary. After filling, the tube is crimped shut, packed and sent to storage, prior to later shipment, sale and use.

In another embodiment of the invention the separating layer, which, as described, is a clear gel, is replaced by the described dentifrice composition less the sodium fluoride, sodium monofluorophosphate and dicalcium phosphate. In still another variation of the invention the separating material is omitted, with the proportions of the dentifrice portions being increased accordingly.

After lengthy storage, over a period of six months, the active (fluoride) content (suitable for hardening tooth enamel and not objectionably insolubilized) is measured, compared to that in a homogeneous dentifrice of the same composition stored the same time. Such content of the experimental formulas will be found to be greater than that of the control. Among the experimental formulas the formulas with a separator, whether of gel or "non-reactive dentifrice", are always of reactive component stability greater than those wherein no such separator is employed.

When the various variations of the formula given above are altered, as in Examples 1-7, the results obtained are like those reported in such examples and in the prior portion of the present example with respect to reactive compound stabilities. Also, when part of the Cab-O-Sil M-5 is included in the gel separator the product is whitened so that the presence of the transparent gel is not as readily detectable.

Although various tube sizes and shapes may be utilized, normally cylindrical tubes of diameters within the range of 1 to 5 cm., preferably 2 to 4 cm., will be employed and the thickness of the deposit of the first portion of dentifrice on the tube wall will usually be within the range of 0.5 to 5 mm., with the thickness of the separator usually being about 0.1 to 1 mm.

When the proportions of the components described in this example are varied, as by ±10%, ±20% and ±30%, within the ranges of proportions given in the preceding specification, similar results are obtainable but care should be taken when thicker deposits of the first dentifrice portion on the tube wall are made (by the method of this example) that these are held in place during subsequent fillings of other materials. In addition to changing proportions of components, the formulations described may also be changed, so as to include other reactive materials, other dentifrice compositions, etc., within the preceding description and similar favorable results for the products of this invention, compared to controls, are obtainable.

EXAMPLE 9

The experiments of Example 8 are repeated but with a different filling mechanism employed, which deposits external stripes of the first dentifrice portion longitudinally along the inner wall of the dentifrice tube, in some cases also depositing separator composition stripes thereover, and which subsequently fills the tube with the first dentifrice portion. In such products the stripes may contain a colorant (appropriate F. D. & C. dye or pigment) to attractively modify the appearance of the dispensed product and to serve as a visual check on the desirable simultaneous extrusion of both components of the dentifrice. The separator portion may be or may not be similarly colored. Such product is also superior in stabilities of the reactive components therein after storage, compared to those of a control.

EXAMPLE 10

Instead of depositing the first dentifrice portion against the wall of the tube and following with central filling of the second portion the first and second portions of the compositions of Example 8 are filled into the tube at the same time by an appropriately modified filling head, with the first portion being deposited as a core inside a surrounding tube of the second portion. In a preferred embodiment of this aspect of the invention an intermediate separating barrier of one of the types previously described is also deposited between the two dentifrice portions. Although it may be more difficult to charge two or three components simultaneously and have them accurately positioned (more difficult compared to the methods described in Examples 8 and 9 supra) there is an advantage in such application because the internal core of the minor component is protected by a thicker layer of separator material when the same weights of the various components of the dentifrice are used. Thus, the thicknesses of the separating layers, with the same formulas, may be from 1 to 5 times as great and stabilities of the reactive materials may be increased accordingly. In any event, on storage, the various products of this example are more stable than those of homogenous controls stored in equal period of time. In all the foregoing examples the "fluoride" present in the dentifrice is useful in hardening tooth enamel and thereby helps to promote dental health.

EXAMPLE 11

The composition of Example 2 is employed in the products of Examples 8-10 and the products made are superior to homogeneous packaged controls in stability of the fluoride component of the dentifrice.

EXAMPLE 12

When the compositions of Examples 4-6 are utilized to make products like those described in Examples 8-11 improved stabilities on storage are also obtained, compared to controls.

EXAMPLE 13

The experiments of Examples 8-12 are repeated but instead of filling a toothpaste tube an aerosol can, pressurized with nitrogen, as described in Example 7, is employed. Whether or not intermediate separators are utilized the products resulting, like those of Example 7, are superior in stabilities of reactive components to controls containing such components mixed together homogeneously but stabilities are increased even more by utilizing the separating barrier layers, as previously described.

In the foregoing examples and in the prior specification various advantages of the invention have been described. However, some of the advantages will be briefly summarized, at least in part, at this time. Because the product is completely extrudable there is no possibility of a non-extrudable separator blocking a dispensing outlet. Utilization of extrudable separators is therefore highly desirable. This is especially true of the embodiment of the invention illustrated in Examples 1-7, wherein a non-extrudable separator could block the outlet openings of the fitting employed and thereby prevent use of some of the material which might still remain in the dentifrice tube. The separator of this invention may be made clear, so that its presence is not obvious or it may be white or colored, as may be considered most appropriate. Although it is desirable for the different portions of dentifrice to be accurately positioned, preferably with a separator between them also being accurately located and covering the "interface" completely to prevent interactions of reactive components in the dentifrice portion and although it is desirable that the products be discharged proportionately from the dispenser, even if there are some dispensing irregularities often these will be of little importance because ultimately the entire composition will be dispensed from the container. Thus, for example, even if discharges of the first and second dentifrice portions of Example 8 are not exactly proportional throughout the dispensing life of the container the total fluoride applied will be a desired quantity over a period of time and for small variations in fluoride proportion ($\pm 50\%$ is even small for such purpose) there is no harmful result and the desirable enamel hardening effect is also obtainable. Similar statements may be made with respect to various other reactive combinations of materials, such as those previously described. However, it is desirable for the materials being dispensed to be of similar flow characteristics so that they will be dispensed together and when the separator is present, so that it too will be dispensed with the dentifrice portions and will maintain its position between them so that it continues to perform as a separator during the useful life of the product.

The invention has been described with respect to various illustrations of preferred embodiments thereof but is not to be limited to these because it is evident that one of skill in the art, with the present specification before him, will be able to utilize substitutes and equivalents without departing from the spirit of the invention.

What is claimed is:

1. A dispensing container of stabilized, extrudable cream, paste or gel dentifrice comprising at least two components which are normally reactive with each other and which are maintained separate from each other in the dispensing container during normal repeated uses of the dentifrice, which container is of a deformable or collapsible tube type, having a closable opening through which the dentifrice is pressure dispensable in response to squeezings of the tube, with the normally reactive components being dispensed together during initial and subsequent dispensings, and in which said components are maintained separate from each other until each dispensing or until shortly before such dispensings by a barrier of extrudable separating material between them, which separating material remains at least in part between the reactive dentifrice components remaining in the container after repeated dispensings and is extrudable through the dispensing opening of the dispensing container together with and as a part of at least some of the dentifrice being dispensed in response to squeezing of the tube.

2. A container of dentifrice according to claim 1 wherein the dispensing opening is in a normally capped neck at the end of the tube.

3. A container of dentifrice according to claim 2 wherein the two reactive components are in separate dentifrice portions with the extrudable separator between them, both of which dentifrice portions are in extrudable paste or gel form, a first portion being from 2 to 49.5%, a second portion being from 50 to 97.5% and the extrudable separator being from 0.5 to 10% of the total weight of said dentifrice portions and said separator, the first dentifrice portion including a reactive component normally reactive with one or more components of the second portion of the dentifrice, which component is in a medium in which it is stable, the second portion including dentifrice constituents, at least one of which is reactive with the reactive component of the first dentifrice portion, the first dentifrice portion being located nearer than the second dentifrice portion to the dispensing opening of the dispensing container and with blending means for bringing said first and second dentifrice portions together before dispensing being located in the container near the dispensing end thereof.

4. A container of dentifrice according to claim 3 wherein the first dentifrice portion is from 5 to 19%, the second dentifrice portion is from 80 to 94% and the separator portion is from 1 to 5% of the total of said dentifrice portions and separator portion, the blending means includes a passageway for dispensing the second dentifrice portion from the container and said passageway includes a wall having at least one opening therein communicating with the first dentifrice portion and through which such first dentifrice portion passes to contact the second dentifrice portion and to be dispensed with it in response to pressure.

5. A container of dentifrice according to claim 4 wherein the blending means includes a tube extending into the dentifrice container, having a main inlet opening therein and an outlet and passing through the container dispensing opening, which tube includes a plurality of openings in a wall thereof at about the same distance from the dispensing opening for passage of the first dentifrice portion through them and into contact with the second dentifrice portion, said openings being located so as to be in contact with the first dentifrice portion during dispensing of the dentifrice and with the main inlet opening of such tube being located as to be in contact with the second portion of the dentifrice during dispensing of dentifrice.

6. A container of dentifrice according to claim 5 wherein one of the dentifrice portions includes a compound which is a source of fluorine useful as a tooth enamel hardening agent or a mixture of such compounds and the other portion contains other components of a dentifrice composition, including at least one component which normally is reactive with said source of fluorine and which inactivates such compound and decreases its utility as a tooth enamel hardening agent when stored in contact with it in a homogeneous dentifrice formulation of the same composition as the present dentifrice.

7. A dispensing container of dentifrice according to claim 6 wherein the first and second portions thereof are of the same color or appearance and have the appearance of a uniform, non-self-contrasting product after being dispensed from the dispensing container.

8. A dispensing container of dentifrice according to claim 7 wherein the openings in the blending means for the passage of the first dentifrice portion into contact with the second dentifrice portion during dispensing are located adjacent to the dispensing container opening and the extrudable separator is present at an interface substantially transverse to the axis of the deformable tube to separate said portions and prevent or diminish any reactions between reactive components thereof at said interface during storage.

9. A container of dentifrice according to claim 3 wherein the extrudable separator is present at an interface substantially transverse to the axis of the deformable tube to separate the reactive dentifrice portions and prevent or diminish any reactions between the reactive components thereof at said interface during storage.

10. A container of dentifrice according to claim 8 wherein the compound which is a source of fluorine useful as a tooth enamel hardening agent is selected from the group consisting of sodium monofluorophosphate and sodium fluoride and mixtures thereof, the reactive compound of the other dentifrice portion is selected from the group consisting of dicalcium phosphate, tricalcium phosphate and calcium carbonate and the separator is a gel of sodium carboxymethyl cellulose in an aqueous polyhydric alcohol vehicle.

11. A container of dentifrice according to claim 9 wherein the compound which is a source of fluorine useful as a tooth enamel hardening agent is selected from the group consisting of sodium monofluorophosphate and sodium fluoride and mixtures thereof, the reactive compound in the other dentifrice portion is a calcium salt and the separator is a gel of a dentifrice gum gelling agent in a dentifrice vehicle.

12. A container of dentifrice according to claim 10 wherein the dentifrice proportion of the compound which is a source of fluorine useful as a tooth enamel hardening agent in the dentifrice (said dentifrice including the separator) is from 0.3 to 2%, the gum or gelling agent content is from 0.5 to 10%, being from 0.5 to 10% in the separator too, the proportion of reactive component, which is a polishing agent, is from 10 to 60%, the proportion of aqueous polyhydric alcohol vehicle, exclusive of water, is 10 to 35%, the glycerol:sorbitol ratio of such vehicle is in the range of 0.3:1 to 10:1 and the moisture content is 8 to 30%.

13. A container of dentifrice according to claim 12 wherein the separator is about 2 to 3% of the contents of the container and is of essentially the same gelling agent-aqueous polyhydric alcohol composition as the rest of the dentifrice.

14. A container of dentifrice according to claim 2 wherein the two reactive components are in separate dentifrice portions concentrically positioned with respect to each other about the longitudinal axis of the deformable tube with the extrudable separator concentrically located between them.

15. A container of dentifrice according to claim 14 wherein both dentifrice portions are in extrudable paste or gel form, a first portion is from 2 to 49.5%, a second portion is from 50 to 97.5% and the extrudable separator is from 0.5 to 10% of the total weight of said dentifrice portions and said separator, the first dentifrice portion includes a component which normally is reactive with one or more components of the second portion of the dentifrice, which component is in a medium in which it is stable, the second dentifrice portion includes dentifrice constituents, at least one of which is reactive with the reactive component of the first dentifrice portion and the first dentifrice portion is located exteriorly of the second dentifrice portion.

16. A container of dentifrice according to claim 15 wherein the first dentifrice portion is from 5 to 19%, the second dentifrice portion is from 80 to 94% and the extrudable separator portion is from 1 to 5% of the total of said dentifrice portions and separator portion.

17. A container of dentifrice according to claim 16 wherein the one of the dentifrice portions includes a compound which is a source of fluorine useful as a tooth enamel hardening agent or a mixture of such compounds and the other portion includes other components of a dentifrice composition, including at least one compound which normally is reactive with said source of fluorine and which can inactivate such compound and decrease its utility as a tooth enamel hardening agent when stored in contact with it in a homogeneous dentifrice formulation of the same composition as the present dentifrice.

18. A container of dentifrice according to claim 17 wherein the compound which is a source of fluorine useful as a tooth enamel hardening agent is selected from the group consisting of sodium monofluorophosphate and sodium fluoride and mixtures thereof, the reactive compound of the other dentifrice portion is selected from the group consisting of dicalcium phosphate, tricalcium phosphate and calcium carbonate and the separator is a gel of sodium carboxymethyl cellulose in an aqueous polyhydric alcohol vehicle.

19. A container of dentifrice according to claim 18 wherein the dentifrice proportion of the compound which is a source of fluorine useful as a tooth enamel hardening agent in the dentifrice includes from 0.3 to 2% of sodium monofluorophosphate and/or sodium fluoride, 0.5 to 10% of sodium carboxymethylcellulose gelling agent, with from 0.5 to 10% of such material also being present in the gelled polyolwater separator, from 10 to 60% of reactive component polishing agent, 10 to 35% of aqueous polyhydric alcohol vehicle, exclusive of water, the glycerol-sorbitol ratio of such vehicle being in the range of 0.3:1 to 10:1 and 8 to 30% of water.

20. A container of dentifrice according to claim 19 wherein the separator is about 2 to 2% of the contents of the container and is of essentially the same gelling agent-aqueous polyhydric alcohol composition as the rest of the dentifrice.

21. a container of dentifrice according to claim 14 wherein the first dentifrice portion is positioned in the container interiorly of the second dentifrice portion with the extrudable separator between such portions.

22. A container of dentifrice according to claim 15 wherein the first dentifrice portion is positioned in the container interiorly of the second dentifrice portion with the extrudable separator between such portions.

23. A method of making a dispensing container of stabilized cream, paste or gel dentifrice comprising at least two components which are normally reactive with each other and which are desirably maintained separate from each other in a tubular dispensing container which comprises applying to the wall of such container over the length thereof a layer of a first dentifrice portion containing one of the reactive components and not the other, applying to the surface of such first portion of dentifrice an extrudable material to cover such surface and filling the balance of the dispensing container with a second portion of such dentifrice containing a second reactive component and not the first reactive component and sealing the container.

24. A method according to claim 23 wherein the container wall is cooled before application of the first dentifrice composition to the interior of said wall so as to cool the first dentifrice composition applied and minimize flow thereof with respect to said wall after application.

25. A method according to claim 24 wherein the dentifrice container is rotated about its axis during application of the first portion of dentifrice so as to promote even application of said dentifrice to the interior wall of said container.

26. A method according to claim 23 wherein separate dentifrice portions, each containing a component reactive with a component of the other portion, are simultaneously filled into the dentifrice container with the first portion, of a lesser weight than the second portion of dentifrice, being in the interior of the container and being separated from the second portion by an extrudable separator.

27. A method for making a dispensing container of stabilized cream, paste or gel dentifrice comprising 5 to 19% of a first portion containing sodium monofluorophosphate and/or sodium fluoride, 1 to 5% of a gel separator extrudable with the dentifrice composition as a part thereof, and the balance of a second dentifrice portion, a component of which is reactive with the sodium monofluorophosphate and/or sodium fluoride of the first dentifrice portion, which comprises preparing separate first and second portions of said dentifrice, each of which contains one of such two components and not the other, filling the first portion through a sealable end of a dentifrice container into the opposite dispensing end of such container, which has a blending fitting at such dispensing end, which fitting has upstream longitudinal and downstream substantially transverse openings therein for passage of dentifrice during dispensing, so that said filled first dentifrice portion is present about the blending fitting so as to communicate with the transverse opening and not communicate with longitudinal opening thereof, adding the extrudable gel separator to cover any exposed surface of the first dentifrice portion, filling the second portion of the dentifrice composition into the container, sealing off the sealable end of the container and storing the container before use of the contents thereof.

* * * * *